US00PP07968P

United States Patent [19]

Katsuo

[11] Patent Number: Plant 7,968

[45] Date of Patent: Sep. 8, 1992

[54] CRAPE-MYRTLE NAMED WHITE FAIRY

[75] Inventor: Kiyoshi Katsuo, Bunsui, Japan

[73] Assignee: Hokeutsu Nohji Co., Ltd., Niigata, Japan

[21] Appl. No.: 533,345

[22] Filed: May 25, 1990

[51] Int. Cl.[5] ..... A01H 5/00
[52] U.S. Cl. ..... Plt./67.3
[58] Field of Search ..... Plt./54, 54.1, 67.3

*Primary Examiner*—Howard J. Locker
*Attorney, Agent, or Firm*—Oblon, Spivak, McClelland, Maier & Neustadt

[57] ABSTRACT

The subject of the present disclosure is a new and distinct variety of crape-myrtle, named 'White Fairy', which is characterized by its yellowish white blooms and its dwarf habit. The new variety is hardy, well-branched and produces a heavy quantity of blooms.

1 Drawing Sheet

BACKGROUND OF THE NEW PLANT

The present invention relates to a new and distinct variety of crape-myrtle, the variety being primarily characterized by yellowish white blooms.

The variety is further characterized by:

Flat-spreading performance having a (hill spread)/(height) ratio of about 2.5, disc-shaped form, dwarf habit (about 30 cm height), heavy branching habit and an extremely numerous amount of blooms.

The new crape-myrtle variety originated in 1985 as a seedling resulting from the crossing of a pair of crape-myrtle plants. The seed parent was 'Summer And Summer', *Lagerstroemia indica* L., which was bred at a research farm in Uchino-cho, Niigata-shi, Niigate-ken, Japan, and the pollen parent was 'Issai-Sarusuberi', *Lagerstroemia indica* L. This crossing was done at the same research farm described above in 1984 with the object of producing plants having flowers of different colors from the seed parent, 'Summer And Summer.' The seed parent, 'Summer And Summer' has been registered under No. 1733 on Aug. 18, 1988, under the Japanese Seed and Seedlings Law. The pollen parent, 'Issai-Sarusuberi' is a well-known and popular crape-myrtle plant and is under no protection, such as a patent or plant variety protection certificate. In 1986, the asexual reproduction of this selected seedling was done by me and under my direction at the same research farm by green shoot cutting. Then, observations were made for 2–4 years of grown plants during 1987–1989. The continuous asexual propagation has demonstrated that the novel characteristics would hold true from generation to generation, appear to be firmly fixed, and are transmitted without change through succeeding propagations.

The new crape-myrtle variety differs from its seed parent and pollen parent in the following ways.

| | New Variety White Fairy | Seed Parent Summer And Summer |
|---|---|---|
| Tree-Performance (hill spread)/(tree height) ratio | flat-spreading 2.5 | flat-spreading 3.0 |
| Tree form | disc | disc |
| Tree height (cm) | dwarf (28.0) | dwarf (20.0) |
| Branching Habit (number of branches on a main trunk) | heavy 14.0 | medium 5.8 |
| Number of inflorescences per one cluster | numerous 13.5 | medium 5.0 |
| Number of flowers per one inflorescence | numerous 69.5 | medium 32.0 |
| Petal color | yellowish white JHS Color Chart 3301 or RHS Colour Chart 155B | strong purplish pink JHS Color Chart 9205 or RHS Colour Chart 68A, 68B, 73A |

-continued

| | Pollen Parent Issai-Sarusuberi |
|---|---|
| Tree-Performance (hill spread)/(tree height) ratio | upright 0.43 |
| Tree form | obovoid |
| Tree height (cm) | shrub (130.0) |
| Branching Habit (number of branches on a main trunk) | sparse 4.4 |
| Number of inflorescences per one cluster | little 3.5 |
| Number of flowers per one inflorescence | medium 26.0 |
| Petal color | vivid red purple JHS Color Chart 9507 or RHS Colour Chart 71B |

The new crape-myrtle variety may be reproduced with ease by stem cuttings. Just after root taking, young shoots come out and spread as growth proceeds. The variety becomes to show full flat-spreading in tree performance and disc shape in tree form, before appearance of flower buds. The tree height of an adult tree is about 30 cm and the hill spread is about 2.5 times the tree height.

The variety shows heavy branching habit and bears numerous flowers and buds. The blooming period of the variety is long, from July to October in Niigata-shi, Niigata-ken, Japan and in similar climate elsewhere. The variety also shows a good cold hardiness and can overwinter well without being supported with a pole even in a snowy area.

BRIEF DESCRIPTION OF THE DRAWINGS

The accompanying drawings show typical specimens of the new variety in color as nearly true as is reasonably possible to make the same in color illustrations of this character. In each instance, the photographs were taken at the same research farm referred to previously in August, 1989.

DETAILED DESCRIPTION OF THE NEW PLANT

Figure 1:
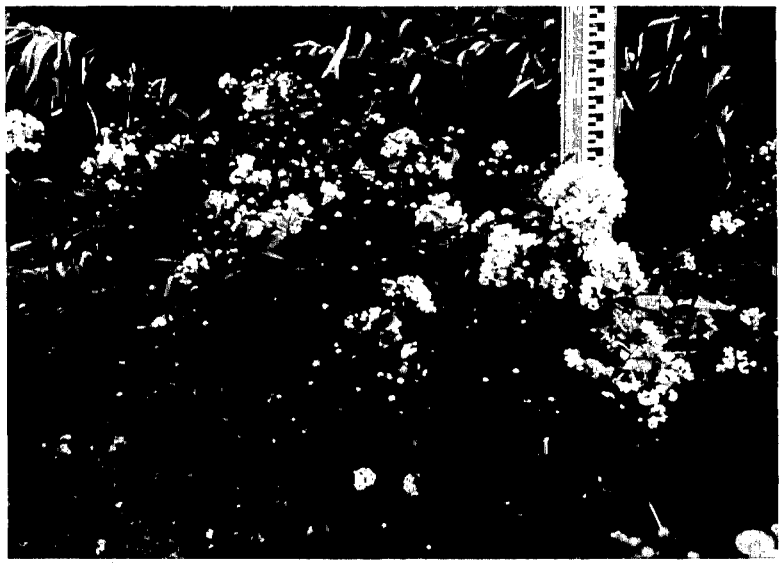
FIG. 1 is a complete view of the new variety together with a scale wherein the dwarf habit of the new variety is apparent.
Figure 2:
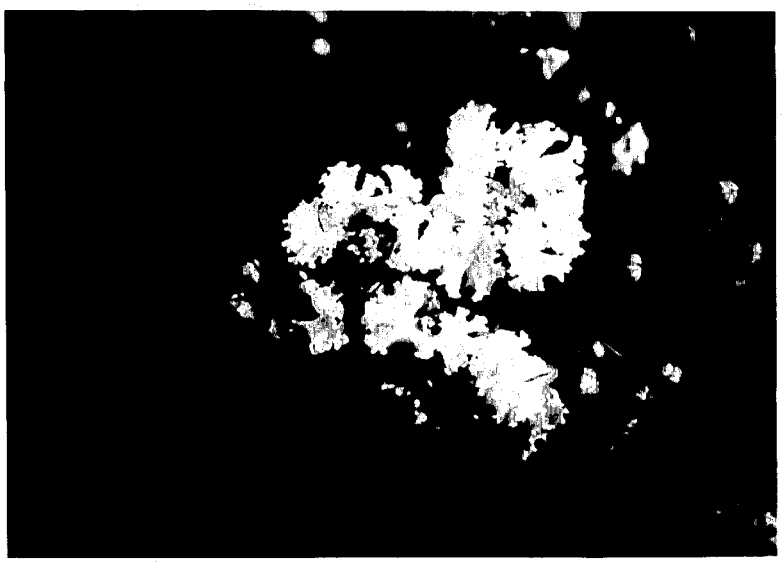
FIG. 2 is a closer view of a blooming peduncle showing the characteristics of the flower and bud.

The following is a detailed description of the characteristics of the new variety as observed at the same research farm noted above. Color designations are made by reference to JHS Color Chart (Japan Horticultural Scale) or R.H.S. Colour Chart (Royal Horticultural Society) except where common terms of color definition are employed.

Plant:

*Tree performance.*—Flat-spreading with a (hill spread)/(tree height) ratio of about 2.5.

*Tree form.*—Disc type.

*Tree height.*—Dwarf, about 25 to 30 cm in adult trees.

Stem:

*Type of trunk.*—Bush.

*Trunk color.*—Purplish brown.

*Young bud.*—Pale red in color.

*Branches.*—Color: Reddish brown. Thickness: 4.1 mm (ave. of 50 shoots). Appearance of branch ridge: Obvious. Branching Habit: Heavy, about 14.0 branches in average on a main trunk. Internode Length: Short, about 1 to 2 cm.

Foliage:

*Average leaf length.*—About 6.2 cm.

*Average leaf width.*—About 3.2 cm.

*Leaflets (lamina).*—Broad lanceolate-shaped.

*Top of Leaflets.*—Acute-shaped (99.0°).

*Base of leaflets.*—Acute-shaped.

*Margin.*—Entire.

*Wave of leaflets.*—None.

*Thickness of leaflets.*—0.4 mm (ave. of 50 leaflets).

*Color of immature leaflets.*—Bright yellow green (JHS Color Chart 3505) or (R.H.S. Colour Chart 149A).

*Color of mature leaflets.*—Upper side is dark green (JHS Color Chart 3716) or R.H.S. Colour Chart 137A, 137B, 147A. under side is dull yellow green (JHS Color Chart 3514) or (R.H.S. Colour Chart 146B, 147B, and 148B).

*Mottling.*—None.

*Color change.*—Red.

*Luster.*—Weakly-glossy finish.

*Hair.*—None on both the upper surface and the under surface.

*Petiole.*—Pale green in color. Length: 1.0 to 1.1 mm.

Flower:

*Pedicel.*—4.5 to 5.5 mm.

*Appearance of calyx tube edge.*—Developed.

*Bud.*—Trapezoidal.

*Cluster.*—Conic-shaped, upward, broad and long.

*Inflorescence.*—Numerous, 13.5 on average per one cluster.

*Semiinflorescence.*—4 to 8 per the lowest inflorescence.

*Number of flowers.*—69.5 on average per one inflorescence.

*Shape or form.*—Single, six petals.

*Fragrance.*—Present, slight.

Petals:

*Color.*—Overall yellowish white (JHS Color Chart 3301) with no variation and slight fading in tone.

*Shape.*—Orbiculate with strong wave.

*Petal base.*—Pale green (JHS Color Chart 4802) in color, and the length of the claw is 8 to 9 mm.

Reproductive organs:

*Style.*—Pale green.

*Pistil.*—One.

*Filaments.*—Yellowish white.

*Anthers.*—Yellow: Yellowish white.

*Stamens.*—30 to 35 arranged around the pistil.

Fruit:

*Shape.*—Ellipsoid, 10 mm. in length (ave. of 50 fruits) and 8.3 mm in width (ave. of 50 fruits), being rotundate on the base and top.

*Color.*—Green in immaturity, and changes to dark purple in maturity.

Growth:

*Habit.*—Dwarf, 25 to 30 cm height.

*First foliage appear.*—April.

*Blooming term.*—July to October.

*Days for bearing flowers.*—About 100.

*Defoliation.*—November.

*Cold hardiness.*—High.

*Heat tolerance.*—High.

*Disease resistance.*—High.

*Pest resistance.*—High.

Species designation: 'White Fairy' is designated as *Lagerstroemia indica* L. hybrid.

The present new variety can survive at a temperature as low as −15° C. and is resistant to *Cercospora lythracearum* Heald et Wolf, generally known as leaf blight.

The following additional descriptive botanical information is also provided:

Bloom diameter: 4.5 to 5.3 cm.

Petal size (width): 1.5 to 1.8 cm.

Persistence of individual blooms: One day from blooming, on the second day after blooming, the flower color begins to fade gradually.

Fertile seeds: Are Observed.

i) Seed color.—dark-grayish brown (JHS Color Chart 1619) or (R.H.S. Colour Chart 200C)

ii) *Samara.*—seed winged at the top.

iii) *Seed size.*—Length: 6.3 mm. (avg. of 50 seeds). Width: 2.9 mm. (avg. of 50 seeds).

iv) *Number of seeds per fruit.*—20 (avg. of 50 fruits).

Tree width: 70.0 cm. (avg. value of 50 plants).

As will be apparent to those skilled in horticultural science, the new variety as herein described may vary in slight detail due to climate, soil and cultural conditions under which the variety may be grown and the stage of growth.

I claim:

1. A new and distinct variety of crape-myrtle plant, substantially as herein described and illustrated.

* * * * *